(12) United States Patent
Warne et al.

(10) Patent No.: US 7,449,444 B2
(45) Date of Patent: *Nov. 11, 2008

(54) HYDROXYETHYL STARCH-CONTAINING POLYPEPTIDE COMPOSITIONS

(75) Inventors: Nicholas W. Warne, Andover, MA (US); Rebecca L. Koval, Billerica, MA (US); John Carpenter, Littleton, CO (US); Theodore W. Randolph, Longmont, CO (US); Suchart Chongpraset, Bangkok (TH)

(73) Assignees: Wyeth, Madison, NJ (US); The Regent of the University of Colorado, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/236,213

(22) Filed: Sep. 27, 2005

(65) Prior Publication Data

US 2006/0079450 A1    Apr. 13, 2006

Related U.S. Application Data

(63) Continuation of application No. 10/390,053, filed on Mar. 17, 2003, now Pat. No. 6,982,080.

(60) Provisional application No. 60/365,044, filed on Mar. 15, 2002.

(51) Int. Cl.
*A61K 38/02* (2006.01)
*A61K 47/26* (2006.01)
*A61K 47/36* (2006.01)

(52) U.S. Cl. ............................. 514/2; 514/777; 514/778

(58) Field of Classification Search ........................ None
See application file for complete search history.

(56) References Cited

U.S. PATENT DOCUMENTS

| | | | |
|---|---|---|---|
| 4,518,584 A | 5/1985 | Mark et al. | 424/85 |
| 4,714,611 A | 12/1987 | Yasaburgo et al. | 424/85 |
| 5,215,895 A | 6/1993 | Bennett et al. | 435/69.52 |
| 5,270,181 A | 12/1993 | McCoy et al. | 435/69.7 |
| 5,292,646 A | 3/1994 | McCoy et al. | 435/69.7 |
| 5,496,830 A | 3/1996 | Shapiro et al. | 514/283 |
| 5,631,219 A | 5/1997 | Rosenthal et al. | 514/6 |
| 5,679,339 A | 10/1997 | Keith et al. | 424/85.2 |
| 5,756,311 A | 5/1998 | Otto et al. | 435/69.51 |
| 5,846,958 A | 12/1998 | Capizzi et al. | 514/114 |
| 6,077,541 A | 6/2000 | Chen et al. | 424/480 |
| 6,126,933 A | 10/2000 | Warne et al. | 424/85.2 |
| 6,174,548 B1 | 1/2001 | Chen et al. | 424/474 |
| 6,207,682 B1 | 3/2001 | Andersen et al. | 514/317 |
| 6,331,316 B1 | 12/2001 | Ullah et al. | 424/482 |
| 6,428,810 B1 | 8/2002 | Bergstrand et al. | 424/480 |
| 6,540,993 B1 | 4/2003 | Warne et al. | 424/85.2 |
| 6,586,573 B1 | 7/2003 | Besman et al. | 530/383 |
| 6,982,080 B2 * | 1/2006 | Warne et al. | 424/85.2 |
| 2004/0057927 A1 | 3/2004 | Warne et al. | 424/85.2 |

FOREIGN PATENT DOCUMENTS

| | | |
|---|---|---|
| WO | WO 91/07495 | 5/1991 |
| WO | WO 92/04455 | 3/1992 |
| WO | WO 93/00807 | 1/1993 |
| WO | WO 96/19574 | 6/1996 |
| WO | WO 99/37322 | 7/1999 |
| WO | WO 00/74707 A2 | 12/2000 |
| WO | WO 01/05355 A2 | 1/2001 |
| WO | WO 02/22156 A2 | 3/2002 |
| WO | WO 03/041637 A2 | 5/2003 |

OTHER PUBLICATIONS

Garzon-Rodriguez et al. *Abstracts of Papers American Chemical Society*, Abstract #14, 221(1-2):pBIOT (2001).
Paul, et al., "Molecular Cloning of a cDNA Encoding Interleukin 11, a Stromal Cell-Derived Lymphopoietic and Hematopoietic Cytokine", *Proc. Natl. Acad. Sci. USA*, 87:7512-7516 (1990).

* cited by examiner

*Primary Examiner*—Jeffrey E Russel
(74) *Attorney, Agent, or Firm*—Ivor R. Elrifi, Esq.; David E. Johnson, Esq.; Mintz, Levin, Cohn, Ferris, Glovsky and Popeo PC

(57) ABSTRACT

The invention provides compositions containing hydroxyethyl starch and polypeptides, including therapeutic polypeptides such as interleukin-11, that provide for enhanced stability of the polypeptide following storage at room temperature or elevated temperatures.

9 Claims, 10 Drawing Sheets

HYDROXYETHYL STARCH-CONTAINING POLYPEPTIDE COMPOSITIONS

RELATED APPLICATIONS

This application is a continuation of U.S. application Ser. No. 10/390,053, filed Mar. 17, 2003, now U.S. Pat. No. 6,982,080, which claims priority to U.S.S.N. 60/365,044, filed Mar. 15, 2002. The contents of the above applications are incorporated herein by reference in their entireties.

STATEMENT OF GOVERNMENT INTEREST

This work was supported by grants by the National Institutes of Health Grant Nos. PHS-T32 CA 79446-02. The government has certain rights in this invention.

FIELD OF THE INVENTION

The invention relates to compositions containing polypeptides, including therapeutic polypeptides such as interleukin-11, that provide for enhanced stability of the polypeptide following storage at room temperature or at elevated temperatures.

BACKGROUND OF THE INVENTION

Recombinant human interleukin-11 (rhIL-11) is a non-glycosylated polypeptide of 177 amino acids. The polypeptide lacks cysteine residues and is highly basic (pI>10.5). rhIL-11 is used as a chemotherapeutic support agent, and is administered in conjunction with other cancer treatments to increase platelet levels. rhIL-11 has also been demonstrated to have anti-inflammatory effects and to be useful in treating conditions such as Crohn's disease. rhIL-11 is a member of a family of human growth factors that includes human growth hormone (hGH) and granulocyte colony-stimulating factor (G-CSF).

To minimize degradation, and to maintain the bioactivity of the polypeptide, preparations containing rhIL-11 and related polypeptides are typically provided as chilled preparations in either a liquid or lyophilized state. Preparing, storing, and transporting the chilled preparations can be labor-intensive, costly and inconvenient for patients and health-care providers.

SUMMARY OF THE INVENTION

The invention is based in part on the discovery of compositions that provide for enhanced stability of polypeptides such as rhIL-11. Combining rhIL-11 with hydroxyethyl starch and either of the disaccharides sucrose or trehalose has been found to result in a composition in which the rhIL-11 is stable following prolonged storage at room temperature. Unless otherwise noted, "room temperature" means 25±5° C.

Any polypeptide for which prolonged storage at or near room temperature is desired can be used in the compositions and methods described herein. In some embodiments, the polypeptide is non-glycosylated, lacks a cysteine residue, and/or has a basic pI.

In one aspect, the invention provides a composition that includes a polypeptide, a disaccharide, and an amylopectin derivative. A preferred amylopectin derivative is a branched amylopectin such as hydroxyethyl starch (HES).

Stability of the polypeptide in the composition can be assessed by storing the composition at elevated temperatures for extended periods of time. For example, the composition is preferably formulated so that the polypeptide is stable for one or more months (e.g., 1, 2, 3, 5, 6, 7, 8, or 9 or more months) when the composition is stored at 60° C.

Preferred disaccharides are trehalose or sucrose. In preferred embodiments, the disaccharide is present in the composition at a concentration of 1.5 to 6.0%. For example, the disaccharide can be present at a concentration of 2.5-5.0%.

The hydroxyethyl starch is preferably present in the composition at a concentration of 0.5 to 3.5%, e.g., the hydroxyethyl starch may be present at a concentration of 2.5%.

In one embodiment, the invention provides a composition that includes rhIL-11, sucrose, and hydroxyethyl starch. The sucrose is present in the composition at a concentration of 2.5% to 5.0%, and the hydroxyethyl starch is present in the composition at a concentration of about 2.5%.

Also provided by the invention is a composition that includes rhIL-11, trehalose, and hydroxyethyl starch. The trehalose is present in the composition at a concentration of 2.5% to 5.0%, and the hydroxyethyl starch is present in the composition at a concentration of about 2.5%.

In a further aspect, the method provides a method of treating or preventing inflammation in a subject by administering to the subject a composition that includes rhIL-11, a disaccharide, and hydroxyethyl starch. In some embodiments, the inflammation is associated with inflammatory bowel disease, such as Crohn's disease.

In one embodiment, the invention includes a method of treating or preventing inflammation in a subject by administering to a subject a composition that includes rhIL-11, sucrose, and hydroxyethyl starch. The sucrose is present in the composition at a concentration of 2.5% to 5.0%, and the hydroxyethyl starch is present in the composition at a concentration of about 2.5%.

Also within the invention is a method of treating or preventing inflammation in a subject by administering to a subject a composition that includes rhIL-11, trehalose, and hydroxyethyl starch, wherein the trehalose is present at a concentration of 2.5% to 5.0%, and the hydroxyethyl starch is present at a concentration of about 2.5%.

The invention further provides a method of enhancing an immune response in, or increasing platelet levels of, a subject by administering to the subject a composition that includes rhIL-11, a disaccharide, and hydroxyethyl starch.

In a further embodiment, the method includes a method of enhancing an immune response in a subject by administering to a subject a composition that includes rhIL-11, sucrose, and hydroxyethyl starch. The sucrose is present in the composition at a concentration of 2.5% to 5.0%, and the hydroxyethyl starch is present in the composition at a concentration of about 2.5%.

In a further aspect the invention includes a method of increasing platelet levels in a subject by administering to the subject a composition that includes rhIL-11, a disaccharide (e.g., sucrose or trehalose), and hydroxyethyl starch. The disaccharide is present in the composition at a concentration of 2.5% to 5.0%, and the hydroxyethyl starch is present in the composition at a concentration of about 2.5%.

The subject used in the herein described methods can be, e.g., a human, a non-human primate, a dog, a cat, horse, cow, pig, sheep, rabbit, rat, or mouse.

Also provided by the invention is a method of making a stable rhIL-11-containing composition. The method includes providing an rhIL-11 polypeptide and contacting the rhIL-11 with a disaccharide and hydroxyethyl starch, thereby making a stable rhIL-11-containing composition. Preferably, the rhIL-11 polypeptide is stable in the composition for at least 1 month when the composition is stored at 60° C. In preferred embodiments, the rhIL-11 polypeptide is stable in the composition for at least 2, 3, 4, 5, 6, 7, 8 or 9 or more months when the composition is stored at 60° C. The disaccharide in the composition is preferably sucrose or trehalose, and is preferably present in the composition at a concentration of 2.5% to 5.0%. The hydroxyethyl starch is preferably present in the composition at a concentration of about 2.5%.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1A shows the spectrum of native rhIL-11 (solid line), protein lyophilized with no excipients (short dash) and 2.5% BES (dash and dot). FIG. 1B shows the spectrum of native rhIL-11 (solid line), protein lyophilized with no excipients (dash and dot), 2.5% sucrose (short dash) and 2.5% trehalose (dotted). FIG. 1C shows the spectrum of native rhIL-11 (solid line), protein lyophilized with no excipients (dash and dot), mixture of 2.5% HES and 2.5% sucrose (short dash), mixture of 2.5% HES and 2.5% trehalose (dotted).

FIG. 2A shows disaccharides (a) 2.5% sucrose, (b) 5.0% sucrose, (c) 5.0% trehalose and (d) 2.5% trehalose formulations. FIG. 2B shows Colyophilized formulations: (e) 5.0% sucrose+2.5% HES (f) 2.5% sucrose+2.5% HES, (g) 5.0% trehalose+2.5% HES, (h) 2.5% trehalose+2.5% HES.

FIG. 3A shows data at 40° C., and FIG. 3B at 60° C.

(FIGS. 4A and C) or 60° C. (FIGS. 4B and D) in the presence of 2.5% sucrose (circle), 5.0% sucrose (triangle down), 2.5% trehalose (square), 5.0% trehalose, (diamond) and 2.5% (w/v) HES (triangle up). FIGS. 4A and B represent the disaccharides or HES formulations and FIGS. 4C and D correspond to the combination of disaccharides with HES.

(FIGS. 5A and C) or 60° C. (FIGS. 5B and D) in the presence of 2.5% sucrose (circle), 5.0% sucrose (triangle down), 2.5% trehalose (square), 5.0% trehalose, (diamond) and 2.5% (w/v) HES (triangle up). FIGS. 5A and B represent the disaccharides or HES formulations and FIGS. 5C and D correspond to the combination of disaccharides with HES.

(FIGS. 6A and C) or 60° C. (FIGS. 6B and D) in the presence of 2.5% sucrose (circle), 5.0% sucrose (triangle down), 2.5% trehalose (square), 5.0% trehalose, (diamond) and 2.5% (w/v) HES (triangle up). FIGS. 6A and B represent the disaccharides or HES formulations and FIGS. 6C and D correspond to the combination of disaccharides with HES.

FIGS. 7A and C show data at 40° C., and FIGS. 7B and D at 60° C.

FIGS. 8A and C show data at 40° C., and FIGS. 8B and D at 60° C.

FIGS. 9A and C show data at 40° C., and FIGS. 9B and D at 60° C.

FIGS. 10A and C show data at 40° C., and FIGS. 10B and D at 60° C.

DETAILED DESCRIPTION OF THE INVENTION

Figure 1:
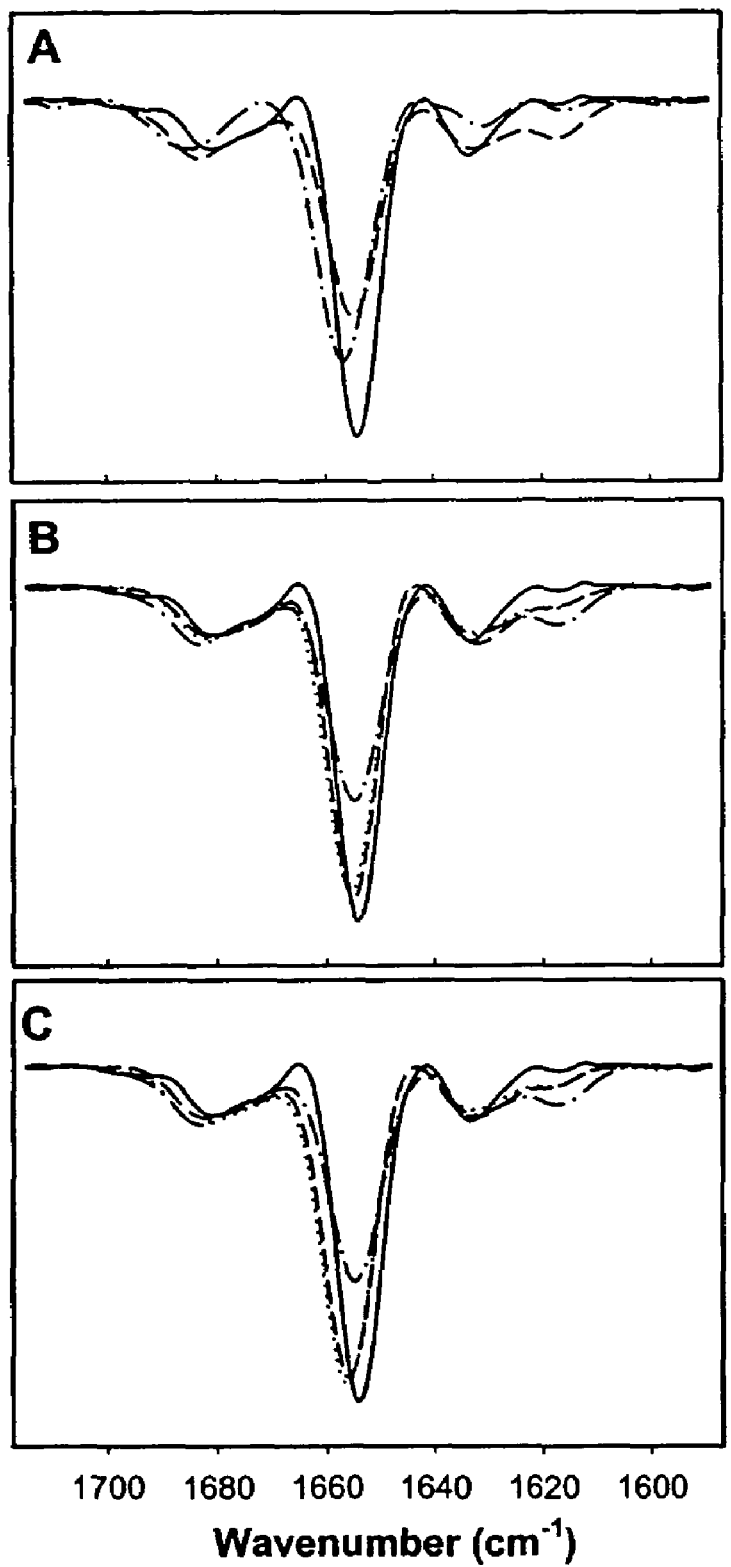
FIG. 1 is an IR spectrum plot showing the second-derivative amide I spectra of rhIL-11 immediately after freeze-drying.

The invention provides compositions that include a polypeptide (e.g., a therapeutically useful polypeptide), a disaccharide and an amylopectin derivative, including branched amylopectins such as hydroxyethyl starch (HES).

Without being limited by any particular mechanism, it is likely that the combination of a hydroxyethyl starch (HES) with a disaccharide, such as sucrose or trehalose, increases the glass transition temperature, $T_g$, of the dried polypeptide compositions of the invention, compared to protein dried with disaccharides alone, and results in improved protein stability during storage.

The invention also provides methods of treating or preventing various disorders, such as inflammatory bowel diseases (e.g., Crohn's disease, ulcerative colitis, indeterminate colitis, and infectious colitis), mucositis (e.g., oral mucositis, gastrointestinal mucositis, nasal mucositis, and proctitis), necrotizing enterocolitis, aphthous ulcers, psoriasis, pharyngitis, esophagitis, peptic ulcers, gingivitis, periodontitis, and ocular diseases (e.g., conjunctivitis, retinitis, and uveitis) in a subject by administering to the subject a composition that includes rhIL-11, a disaccharide, and hydroxyethyl starch.

Interleukin 11 (IL-11) is a pleiotropic cytokine that stimulates primitive lymphohematopoietic progenitor cells and acts in synergy with other hematopoietic growth factors to stimulate the proliferation and maturation of megakaryocytes. IL-11 is described in detail in International Application PCT/US90/06803, published May 30, 1991; as well as in U.S.

Pat. No. 5,215,895; issued Jun. 1, 1993. A cloned human IL-11 was previously deposited with the ATCC, 10801 University Boulevard, Manassas, Va. 20110-2209, on Mar. 30, 1990 under ATCC No. 68284. Moreover, as described in U.S. Pat. No. 5,270,181; issued Dec. 14, 1993; and U.S. Pat. No. 5,292,646; issued Mar. 8, 1994; IL-11 may also be produced recombinantly as a fusion protein with another protein. IL-11 can be produced in a variety of host cells by resort to now conventional genetic engineering techniques. In addition, IL-11 can be obtained from various cell lines, for example, the human lung fibroblast cell line, MRC-5 (ATCC Accession No. CCL 171) and Paul et al., the human trophoblastic cell line, TPA30-1 (ATCC Accession No. CRL 1583). Described in Proc Natl Acad Sci USA 87:7512 (1990) is a cDNA encoding human IL-11 as well as the deduced amino acid sequence (amino acids 1 to 199). U.S. Pat. No. 5,292,646, supra, describes a des-Pro form of IL-11 in which the N-terminal proline of the mature form of IL-11 (amino acids 22-199) has been removed (amino acids 23-199). As is appreciated by one skilled in the art, any form of IL-11 that retains IL-11 activity is useful according to the present invention.

In addition to recombinant techniques, IL-11 can also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof, which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins that may be employed in the compositions and methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. (See, e.g., U.S. Pat. No. 4,518,584.)

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions (Sambrook et al., Molecular Cloning. A Laboratory Manual, 2d edit., Cold Spring Harbor Laboratory, New York (1989)) will be similarly useful in this invention.

Also considered useful in the compositions and methods disclosed herein are fusion molecules, prepared by fusing the sequence or a biologically active fragment of the sequence of one cytokine to another cytokine or proteinaceous therapeutic agent, e.g., IL-11 fused to IL-6 (see, e.g., methods for fusion described in PCT/US91/06186 (W092/04455), published Mar. 19, 1992). Alternatively, combinations of the cytokines may be administered together according to the method.

Thus, where in the description of the methods of this invention IL-11 is mentioned by name, it is understood by those of skill in the art that IL-11 encompasses the protein produced by the sequences presently disclosed in the art, as well as proteins characterized by the modifications described above yet which retain substantially similar activity.

Hydroxyethyl Starch (HES)

While any branched polysaccharide (e.g., an amylopectin) can be used in the compositions and methods described herein, HES is a preferred stabilizer because it is non-toxic, is biodegradable, has excellent glass-forming properties, and is clinically approved for therapeutic uses.

Hydroxyethyl starch is a derivative of amylopectin, which is a highly branched compound of about 250-300 K that is soluble in water and virtually insoluble in organic solvents. HES includes about 0.4 to about 0.5 hydroxyethyl units per component glucose monomer. In humans and other animals, amylopectin is rapidly hydrolyzed by alpha-amylase. The activity of alpha-amylase depends on the position of the hydroxyethyl groups at positions C2, C3, and C6 on the glucose molecule. HES can be obtained from a variety of vendors.

Disaccharides

Preferred disaccharides are sucrose and trehalose. Disaccharides can be obtained from a variety of vendors.

Preparing Compositions that Include a Polypeptide, Disaccharide, and Hydroxyethyl Starch Compositions containing a polypeptide, disaccharide and hydroxyethyl starch can be prepared by buffer exchanging the polypeptide into the appropriate solution. This process can be accomplished, by one skilled in the art, by diafiltration, dialysis, chromatography, crystallization followed by reconstitution or some combination of freeze-drying or spray-drying followed by reconstitution with water or a combination of water and disaccharides and/or hydroxyethyl starch. Once the solution containing the polypeptide, disaccharide and hydroxyethyl starch has been prepared, it is dehydrated by means of freeze-drying, spray-drying, vacuum drying or by the use of supercritical fluid based dehydration. The resultant lyophilized powder represents the stable composition of the polypeptide, disaccharide and hydroxyethyl starch.

Methods of Treatment with IL-11

A suitable treatment regimen for patients undergoing treatment, including for example prophylactic treatment, may be determined by the attending physician based upon such factors as the patient's age, sex, weight, and general health. Generally, a suitable dose of IL-11 ranges broadly, preferably between 1 and 100 µg/kg body weight, e.g., 5 to 90 µg/kg body weight. 10 to 80 µg/kg body weight, 20 to 70 µg/kg body weight, or 30 to 65 µg/kg body weight. Another suitable dose is in the range of about 25 to 50 µg/kg body weight. If desired, these doses can be adjusted to units. A unit is conventionally described as the concentration of polypeptide which leads to half-maximal stimulation in a suitable assay, e.g., for IL-11, the T1165 assay described in PCT/US90/06803. Doses may be administered daily for between one day and six months, or for as long as is deemed necessary and safe, as is readily ascertained by standard tests by the attending physician, depending upon the nature of the disorder being treated. Where appropriate, the dosages may be adjusted upward or downward, for example, a dosing regimen requiring administration of IL-11 at a dose of 25 µg/kg, daily for one week, or fewer days, or multiple weeks if indicated. The progress of treatment is appropriately monitored by measurement of markers associated with the disorder being treated to determine if such a dose results in a decrease of, for example, TNFα levels (or corresponding marker) and if not, increasing the dose two-fold for an additional time period of treatment and measurement of marker levels until an effective dosing regimen is reached.

Compositions of the invention may be administered rectally, parenterally, intracisternally, intravaginally, intraperitoneally, bucally, or as a nasal spray. The term "parenteral" as used herein refers to modes of administration that include intravenous, intramuscular, intraperitoneal, intrasternal, subcutaneous and intraarticular injection and infusion.

EXAMPLES

The invention will be further illustrated in the following non-limiting examples. The examples describe the prediction of protein stability in a dried solid after formulation and lyophilization of composition that includes the polypeptide, hydroxyethyl starch (HES), and sucrose or trehalose (Example 1). Also shown are examples describing IL-11 properties in compositions after short-term storage (Example 2), and long-term storage nine months at three different temperatures (Example 3).

In some examples, protein stability was predicted by measuring the $T_g$ of the lyophilized cake. The $T_g$, or glass transition temperature, is a temperature range over which a material undergoes a transformation from a glass state to rubbery texture state and undergoes a change in mobility. The $T_g$-glass transition is a useful indicator of the stability of a lyophilized polypeptide-containing composition: a low $T_g$-glass transition temperature indicates a relatively unstable lyophilized composition. The $T_g$ temperature was determined using differential scanning calorimetry (DSC).

Protein structure was determined using infrared spectroscopy, size exclusion high performance liquid chromatography (SEC-HPLC) and reversed phase high performance liquid chromatography (RP-HPLC).

Example 1

Preparation and Screening of Compositions Including IL-11, a Disaccharide and/or Hydroxyethyl Starch Materials and Methods Materials Recombinant Human Interleukin-11 (rhIL-11) was produced at Wyeth BioPharma (Andover, Mass.). The protein was expressed in *Escherichia coli* as a part of a fusion protein with a thioredoxin, from which it was cleaved and purified to homogeneity using conventional chromatography as previously reported. (Czupryn et al., J Biol Chem. 270, 978-985 (1995)). Sucrose and trehalose were purchased from Pfanstiehl laboratories (Waukegan, Ill.). Hydroxyethyl starch HES (Viastarch) was purchase from Fresenius, Austria, and had a mean molecular weight of 200 kD. (Searles et al., J Pharm Sci. 90, 860-871 (2001)). All other reagents were obtained from Sigma Chemicals Co. (St. Louis, Mo.).

Lyophilization

Samples were freeze-dried with a FIS Durastop lyophilizer equipped with a Dura dry MP condenser unit (Stone Ridge, N.Y.). (Allison et al., J. Pharm. Sci. 89,199-214 (2000)). Formulations of rhIL-11 were prepared in 10 mM Tris buffer pH 7.0 to a final protein concentration of 3.9 mg/mL, with sucrose (1.0, 2.5, 5.0 or 10.0% wt/vol), trehalose (1.0, 2.5, 5.0 or 10.0%) or HES (2.5%). Formulations containing 2.5% HES with 1.0, 2.5, 5.0 or 10.0% disaccharide were also prepared. Samples aliquots (1 mL) were transferred into 5 mL lyophilization vials (West Co.) and placed on the lyophilizer shelf, which was at room temperature.

Samples were frozen by cooling the shelves to −40° C. at a rate of 2.5° C./min. After the samples were at this temperature for 4 hours, primary drying was started by reducing chamber pressure to 100 µmHg, and continued by maintaining the shelf temperature at −40° C. for 48 hours. Secondary drying (100 µmHg chamber pressure) was initiated by increasing shelf temperature to 25° C. at a rate of 2° C./min. This temperature was maintained for 12 hours. This lyophilization conservative cycle was designed to assure that the formulations containing disaccharides alone as excipients did not collapse during processing. All formulations formed pharmaceutically elegant cakes. The residual water content of all formulations were 0.5-0.9% by mass as determined by Karl-Fisher titration. (Allison et al., J. Pharm. Sci. 89,199-214 (2000)).

Storage Stability

After lyophilization, the vials were sealed under vacuum and placed in incubators at 40 and 60° C. Samples of each formulation were removed at the indicated time points and stored at −20° C. until analyzed.

Differential Scanning Calorimetry

Thermal analysis of dried Interleukin-11 formulations was performed using a Perkin-Elmer DSC-7 differential scanning calorimeter (Norwalk, Conn.). Dried samples (5 mg) were sealed in aluminum sample pans in a dry nitrogen-purged glove box, and analyzed with an empty pan in the reference oven. Samples were warmed at 5° C./min, and thermal data were obtained. Samples were scanned twice. (Hatley, Develop Biol Standard. 74, 105-122 (1991)). During the first scan, samples were heated to the onset of the $T_g$ and cooled to 0° C. During the second scan the sample was heated to 190° C., and the $T_g$ value was determined. Glass transition temperatures were reported as the midpoint in the second-order transition in the baseline. The results are presented as approximate average values for triplicate samples as shown in Table 1.

TABLE 1

| Amorphous Component | Percent Hydroxyl Ethyl Starch | |
|---|---|---|
| | None | 2.5% |
| None | 140° C.[a] | ND |
| 1% sucrose | 65.0° C. | ND |
| 2.5% sucrose | 60.8 ± 3.8° C. | 83.7 ± 3.2° C. |
| 5% sucrose | 60.7 ± 4.5° C. | 80.1 ± 5.7° C. |
| 10% sucrose | 55° C. 65° C. | |
| 1% trehalose | 75° C. | ND |
| 2.5% trehalose | 103.7 ± 1.9° C. | 124.7 ± 4.5° C. |
| 5% trehalose | 104.3 ± 4.6° C. | 119.7 ± 2.8° C. |
| 10% trehalose | 103° C. | 115° C. |

[a]temperature calculated was a melting temperature, not a $T_g$.
ND = no glass transition detectable.

Figure 2:
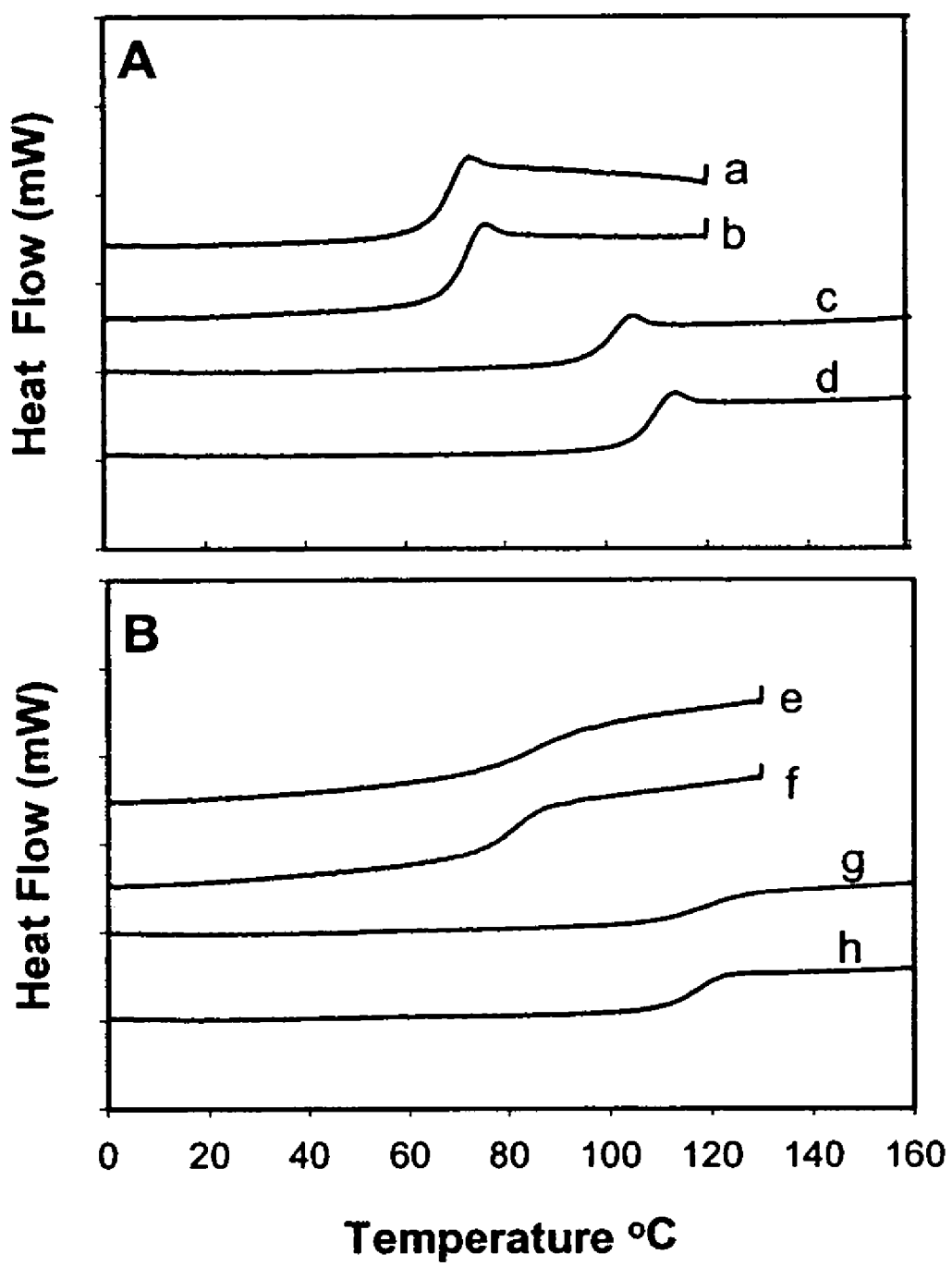
FIG. 2 is a representative DSC thermogram.

The thermograms for the lyophilized formulations containing either disaccharides alone or disaccharide/HES mixtures had a single observable glass transition (FIG. 2). As expected, the $T_g$ values for formulations with sucrose alone were substantially lower than those for formulations with trehalose alone (Table I above). (Duddu and Monte, Pharm. Res. 12, 1250-1259 (1997)). The $T_g$ values for trehalose formulations were well above the temperatures (40 and 60° C.) employed in the storage stability described below. In contrast, the $T_g$ values for the sucrose formulations were around 60° C. The $T_g$ values were based on the midpoint of the glass transition event in the thermogram, which were determined on the timescale of minutes. Clearly, the transition from the glassy to the rubbery states occurs at a lower temperature, and hence, during long-term storage at 60° C., the formulations in sucrose alone will not be in a glassy state. Thus, although both sucrose and trehalose formulations meet the criterion for long-term storage stability of prevention of protein unfolding during lyophilization, with the sucrose formulation the second criterion for storage at a temperature below $T_g$ will not be met during storage at 60° C.

For the lyophilized rhIL-11 formulation with 2.5% HES alone a glass transition could not be detected in the thermogram. HES is a relatively large carbohydrate polymer (mean molecular weight of 200 kD) and is expected to have a $T_g$ near that of similarly sized unmodified starches (e.g., >120° C.) that is substantially greater than that for sucrose or trehalose. (Hageman, Water sorption and solid state stability of protein. In stability of protein pharmaceutical. Part A. Chemical and physical pathways of protein degradation; Aher, T. J. Manning, M. C., Eds.; Plenum press: New York: pp 273-309 (1992) and To and Flink, J Food Technol. 13, 567-581 (1978)). With both sucrose and trehalose formulations, the presence of 2.5% HES raised the formulations' $T_g$ about 15-20° C., to well above the highest storage temperature of 60° C. The increased $T_g$ in disaccharide formulations prepared in HES is because the $T_g$ of a large polymer such as HES is substantially higher than that of a disaccharide. Because these formulations also preserved the native protein secondary structure after lyophilization, it is predicted that they will provide the greatest stability, of the formulations tested, to rhIL-11 during storage at both 40 and 60° C.

Infrared Spectroscopy

Infrared spectroscopy was used to study protein secondary structure in the dried formulations immediately after lyophilization and as a function of storage in the dried solid at 40 and 60° C. In a dry nitrogen-purged glove box, dry protein samples (approximately 0.5 mg protein) were mixed with 300 mg KBr. The mixture was ground and then pressed into a pellet at 12,500 PSI. This procedure for preparing KBr pellets does not alter the structure of proteins in the dry solid. (Prestrelski et al., Biophys J. 65, 661-671 (1993)). Aqueous solutions of native rhIL-11 (20 mg/mL) were placed into a cell fitted with $CaF_2$ windows and path length of 6 μm (Biotools, Ill.). Spectra were acquired with a Bomem MB series spectrometer and processed as previously described. (Prestrelski et al., Biophys J. 65, 661-671 (1993); Allison et al., J. Pharm. Sci. 89,199-214 (2000); Chang et al., Arch Biochem Biophys. 331, 249-258 (1996); Kreilgaard et al., J Pharm Sci. 8, 281-290 (1999); Allison et al., Arch Biochem Biophys. 358,171-181 (1998); and Allison et al., Arch Biochem Biophy. 365, 289-298 (1999)). Second-derivative spectra in the conformationally sensitive amide I region were normalized for area and overlaid. (Kendrick et al., J Pharm Sci. 85, 155-158 (1996)).

Infrared spectroscopy was used to assess the effects of the excipients on lyophilization-induced protein unfolding. The second derivative spectrum for native rhIL-11 in the conformationally-sensitive amide I region is dominated by a band at 1656 $cm^{-1}$ for α-helix (FIG. 1). In the spectrum for the protein lyophilized in buffer alone, this band was reduced in intensity concomitant with increased absorbance at around 1623 and 1690 $cm^{-1}$, which is due to an increase in β-sheet content (FIG. 1A). These results document that in the absence of a stabilizing excipient, rhIL-11's secondary structure was perturbed during freeze-drying; native α-helix was lost and non-native β-sheet structure was formed. When the protein was lyophilized in the presence of 2.5% (w/v) HES, lyophilization-induced unfolding was only partially inhibited (FIG. 1A). This observation is consistent with earlier results in which it was shown that another carbohydrate polymer, dextran, could not fully inhibit protein unfolding during freeze-drying. (Allison et al., J Pharm Sci. 89, 199-214 (2000); Kreilgaard et al., J Pharm Sci. 8, 281-290 (1999); Prestrelski et al., Pharm Res. 12, 1250-1259 (1995) and Kreilgaard et al., Arch Biochem Biophys. 360,121-134 (1998)). In contrast, second derivative infrared spectra of rhIL-11 lyophilized from solutions of 2.5 or 5% (w/v) sucrose or trehalose (FIGS. 1B and C) were native-like immediately after lyophilization. The major band at 1656 $cm^{-1}$ in the spectrum of the native protein in aqueous solution was retained in the spectra of the protein lyophilized in trehalose or sucrose. Furthermore, formulations lyophilized in the presence of HES-disaccharide mixtures had infrared spectra that were as similar to the spectrum of the native protein as were the spectra of the protein lyophilized in disaccharide alone (FIGS. 1B and C). Thus, even in the presence of HES, sucrose and trehalose can inhibit lyophilization-induced unfolding of rhIL-11.

Example 2

Assessment of Short-Term Stability of Compositions Containing IL-11, HES, and Sucrose or Trehalose Compositions containing 2.5% HES and 0, 1, 2.5, 5, or 10% sucrose or trehalose were prepared. The percentage of multimer formation and $Met_{58}OX$ was determined after one or two weeks of storage of the formulations at 60° C.

Figure 4:
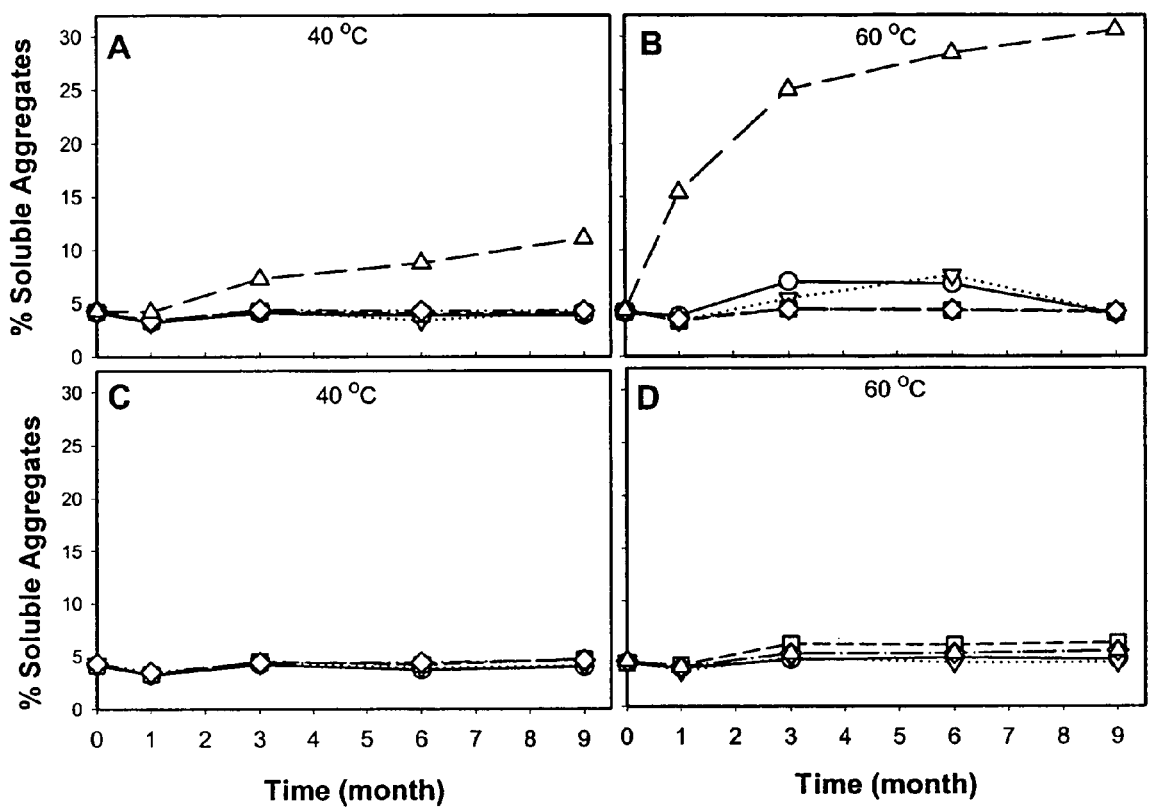
FIG. 4 is a plot showing the formation of soluble aggregates of rhIL-11 as a function of time as determined by size exclusion chromatography. Formulations stored at 40° C.
Figure 5:
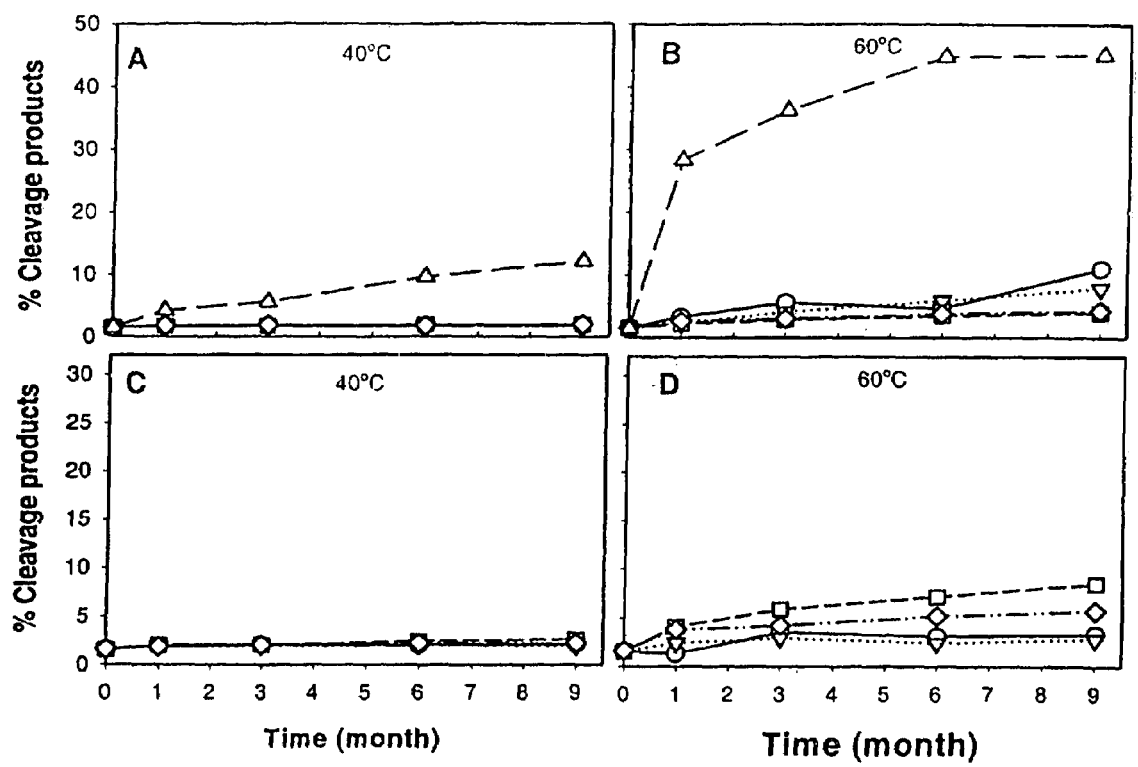
FIG. 5 is a plot showing the formation of cleavage products of rhIL-11 as a function of time as determined by reversed phase chromatography. Formulations stored at 40° C.

Stored samples were rehydrated in 10 mM Tris buffer (pH 7.0) to a final protein concentration of approximately 4.0 mg/ml. Size exclusion chromatography (SEC) was used to measure the levels of soluble aggregates. Analysis was performed using a Waters HPLC system equipped with a Toso-Haas TSK-2000 $SW_{XL}$ column maintained at 5° C. Isocratic elution was performed for 20 minutes at 1.0 mL/min. The mobile phase was 50 mM MES, 0.1 mM Glycine, and 0.5M NaCl (pH 6.0). UV detection was performed at 225 nm. Peak areas in the chromatogram were used to quantify the amounts of soluble aggregates in rehydrated samples For 2.5 and 5% trehalose and sucrose formulations, protein aggregates and cleavage products were not detected after storage at 40° C. and rehydration (FIGS. 4 and 5). Aggregates were also not detected in the trehalose formulations stored at 60° C., but were noted in sucrose formulations (FIG. 4), consistent with the structural perturbations arising in the dried solid. There was only minor cleavage product generation during storage of the disaccharide formulations at 60° C.

Figure 6:
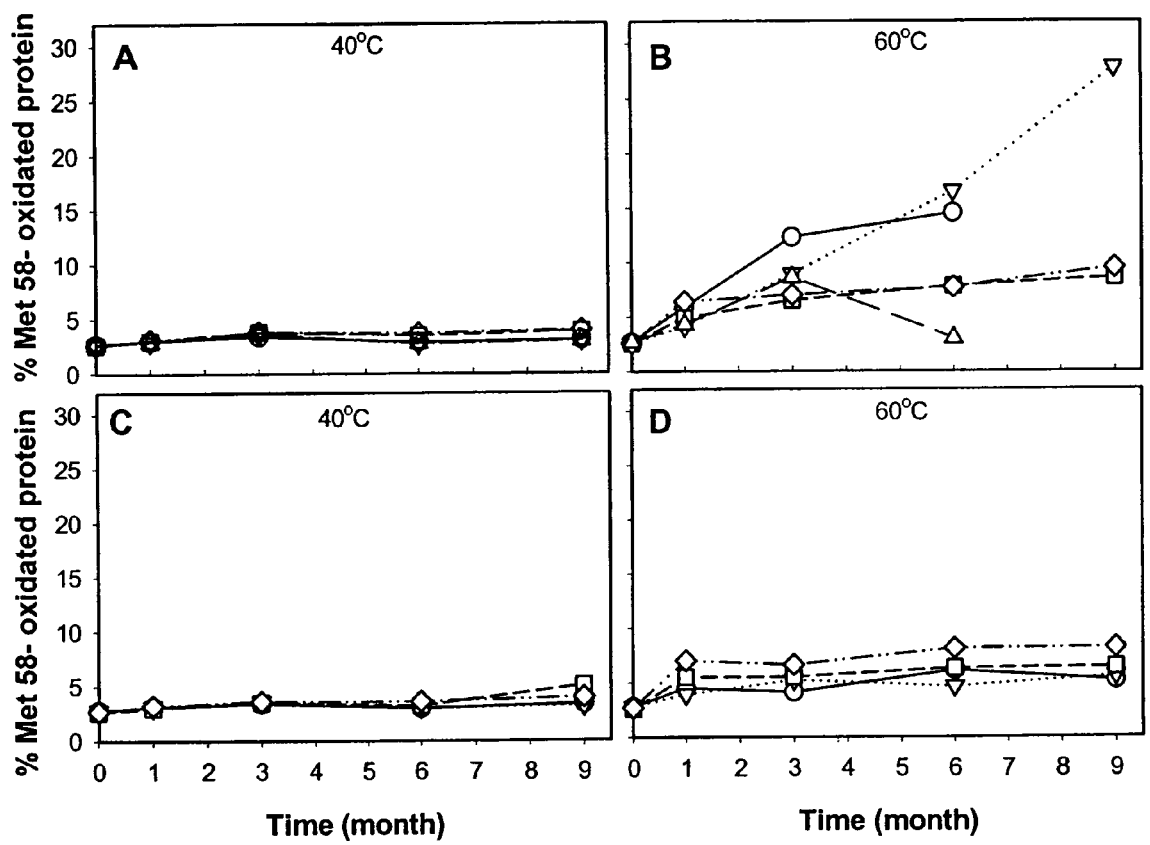
FIG. 6 is a plot showing methionine 58 oxidation of rhIL-11 as a function of time as determined by reversed phase chromatography. Formulations stored at 40° C.

Oxidation of Met-58 did not occur in 2.5 or 5% trehalose and sucrose formulations during storage at 40° C. (FIG. 6), but was detected during storage at 60° C. The amount of oxidation occurring at 60° C. did not appear to correlate with the $T_g$ of the formulation, suggesting that mobility of reactive oxygen species may not be coupled to the glassy state in disaccharide-protein formulations.

Proteins reconstituted from 10% sucrose or 10% trehalose were found to be unstable. Proteins reconstituted from 10% sucrose showed higher levels of multimers (had lower Tg).

Example 3

Assessment of Long-Term Stability of Compositions

Formulations were prepared using the ingredients described below and protein structure was analyzed after lyophilization and storage for up to nine months at different temperatures (5° C., 40° C., and 60° C.) with infrared spectroscopy, DSC, and after rehydration by SEC-HPLC and RP-HPLC.

Determination of $T_g$ of Compositions Including IL-11, a Disaccharide and Hydroxyethyl Starch Using Differential Scanning Calorimetry.

DSC was performed on IL-11 containing formulations with the excipients indicated in Table 2. $T_g$ is taken as the midpoint of a glass transition region, and was determined by measuring the change in heat flow $T_g$ is taken as the mid-point temperature of a glass transition region (mW) at increasing temperatures. The texture (glassy or non-glassy) of the formulation was also noted.

TABLE 2

| Excipient Added to Formulation | $T_g$ (° C.) | Glassy |
|---|---|---|
| 2.5% Sucrose | 65 | Yes |
| 5.0% Sucrose | 65 | Yes |
| 2.5% Trehalose | 105 | Yes |
| 5.0% Trehalose | 110 | Yes |
| 2.5% Hydroxyethyl Starch | ND | — |
| 2.5% Sucrose/2.5% HES | 80 | Yes |
| 5.0% Sucrose/2.5% HES | 75 | Yes |
| 2.5% Trehalose/2.5% HES | 125 | Yes |
| 5.0% Trehalose/2.5% HES | 120 | Yes |

All freeze-dried formulations tested were observed to be in a glassy state. The $T_g$ range extended from 60° C. in pure sucrose systems, to about 120° C.-125° C. in IL-11 that was lyophilized in the presence of trehalose. No $T_g$ was observed in IL-11 lyophilized in the presence of only HES. The presence of HES along with a disaccharide increased the Tg of the dried power relative to that measured for a formulation lyophilized with only disaccharides (sucrose or trehalose). The $T_g$ for all formulations did not change on storage for 9 months relative to $T_g$ measured immediately after lyophilization (Table I), with two exceptions. Glass transitions for the formulations containing 2.5% and 5.0% sucrose at 60° C. were not observed during storage and the cakes collapsed completely. DSC analysis of the collapsed cakes showed a melting peak for crystalline sucrose. Storage of the sucrose formulations at a temperature above $T_g$ resulted in crystallization of the sugar.

Determination of IR-Spectra of Compositions Including IL-11, a Disaccharide and Hydroxyethyl Starch The structure of rhIL-11 in various compositions containing a disaccharide and/or the carbohydrate polymer hydroxyethyl starch (HES) was determined by examining the amide I band at 1600-1700 cm$^{-1}$. Samples whose spectra were measured, and the temperatures at which they were stored, included the following: 2.5% sucrose (40° C. and 60° C.); 2.5% trehalose (40° C. and 60° C.); and 2.5% HES (40° C.).

Figure 3:
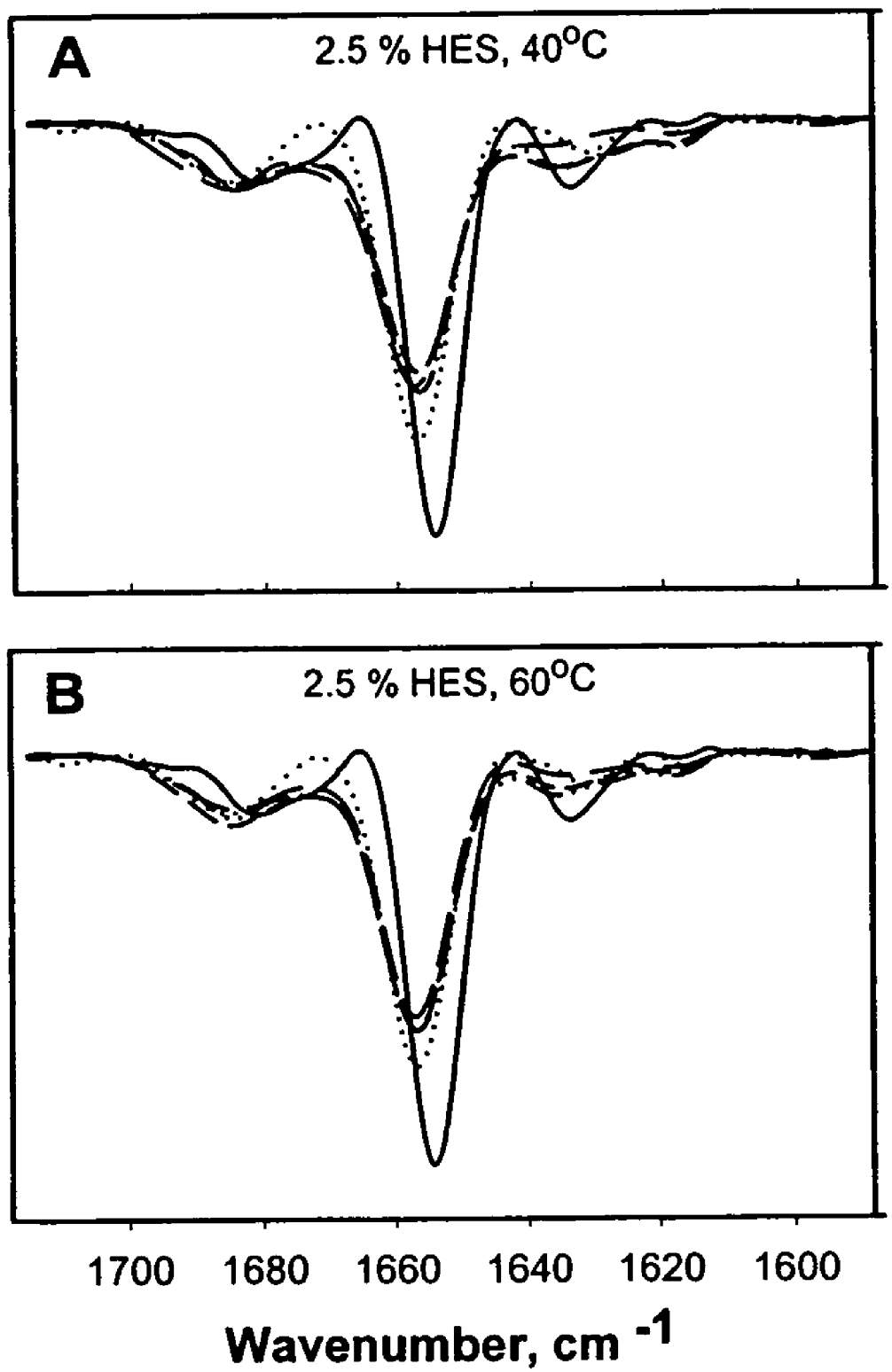
FIG. 3 is an IR spectrum plot showing the second-derivative amide I spectra of rhIL-11 lyophilized with 2.5% (w/v) HES: (solid) native rhIL-11, (dotted) spectra taken immediately after freeze-drying, (dashed) spectra taken after 3 months, (dot-dashed) after 6 months, (long dashed) after 9 months.

Storage Stability of rhIL-11 Dried with HES Alone rhIL-11 was freeze-dried with 2.5% (w/v) HES alone to test the hypothesis that even if a polymeric carbohydrate excipient has a high glass transition temperature it will not provide optimal storage stability to a dried protein, if it does not also prevent protein unfolding during lyophilization. First, to determine if alterations in the protein's secondary structure were occurring during storage in the dried solid, infrared spectra for rhIL-11 in the dried formulations stored at 40 and 60° C. were compared to the spectrum for the formulation immediately after lyophilization. Spectra of the protein in the samples stored for 3 months at both temperatures had a small decrease in the intensity of the α-helix band, indicating a minor, further structural perturbation of the protein during storage in the dried solid (FIG. 3). Further alterations in the structure of the dried protein were not apparent during subsequent analysis of stored dried samples at 6 and 9 months (FIG. 3). The cause for the change in structure that appears to be restricted to the early phase of the storage period is not known. Speculatively, there may be a structural relaxation in the glassy matrix that is complete within the earlier phases of storage and to which a perturbation of protein secondary structure is coupled.

In contrast to the minor secondary structural changes arising during storage, there was great degradation of the stored protein detected after rehydration. Soluble aggregates and cleavage product levels slowly increased in samples stored at 40° C. In samples stored at 60° C., these degradation products reached high levels after only one month of storage. Smaller increases were noted with up to six months of storage, after which degradation appeared to reach a plateau. Levels of oxidized methionine-68 did not increase in samples stored at 40° C., but did increase linearly with time in samples stored at 60° C.

The failure of HES alone to provide storage stability to lyophilized rhIL-11 is consistent with earlier studies that showed that dextran (another high molecular carbohydrate polymer) also did not inhibit lyophilization-induced unfolding (Allison et al., J Pharm Sci. 89, 199-214 (2000); Kreilgaard et al., J Pharm Sci. 8, 281-290 (1999); Prestrelski et al., Pharm Res. 12, 1250-1259 (1995) and Kreilgaard et al., Arch Biochem Biophys. 360,121-134 (1998)) and protein degradation reactions during storage in the dried solid. (Allison et al., J Pharm Sci. 89, 199-214 (2000); Kreilgaard et al., J Pharm Sci. 8, 281-290 (1999); Prestrelski et al., Pharm Res. 12, 1250-1259 (1995); Kreilgaard et al., Arch Biochem Biophys. 360,121-134 (1998) and Pikal et al., Pharm. Res. 8, 427-436 (1991)). Overall, the results of the current and previous studies document that storage of an unfolded protein in a glassy polymeric carbohydrate matrix alone is not sufficient to assure inhibition of degradation in the dried solid.

Storage Stability of rhIL-11 Dried with Sucrose or Trehalose Alone

Figure 7:
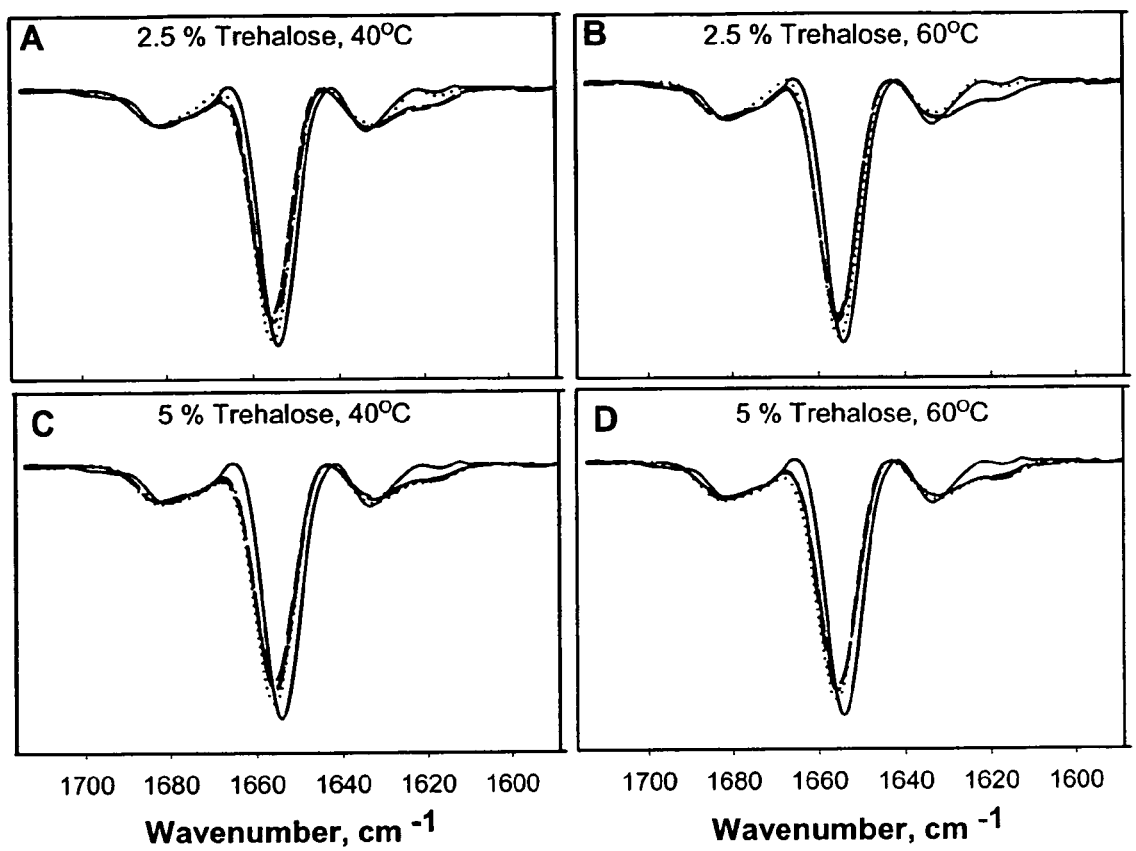
FIG. 7 is an IR spectrum plot showing the second-derivative amide I spectra of rhIL-11 lyophilized with 2.5% trehalose (FIGS. 7A and B) and 5.0% trehalose (FIGS. 7C and D): (solid) native rhIL-11, (dotted) spectra immediately after freeze-drying, (dashed) spectra taken after 3 months, (dot-dashed) after 6 months, (long dashed) after 9 months.
Figure 8:
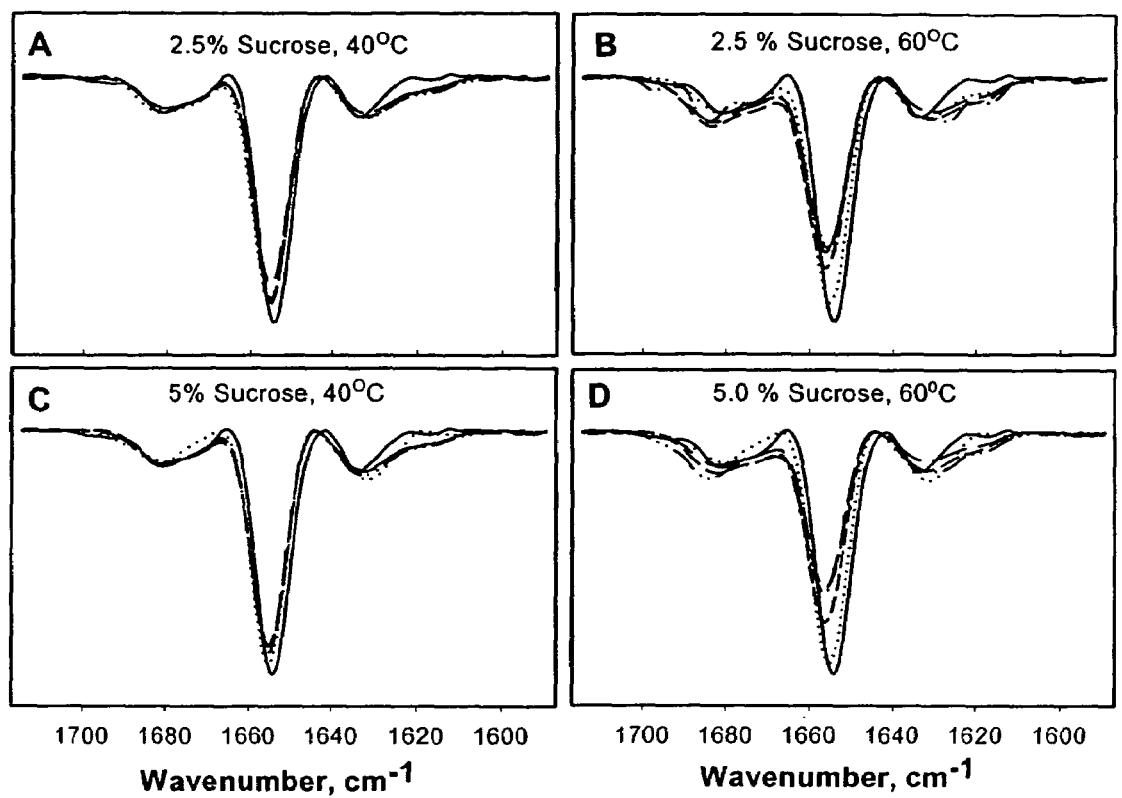
FIG. 8 is an IR spectrum plot showing the second-derivative amide I spectra of rhIL-11 lyophilized with 2.5% sucrose (FIGS. 8A and B) and 5.0% sucrose (FIGS. 8C and D): (solid) native rhIL-11, (dotted) spectra immediately after freeze-drying, (dashed) spectra taken after 3 months, (dot-dashed) after 6 months, (long dashed) after 9 months.
Figure 9:
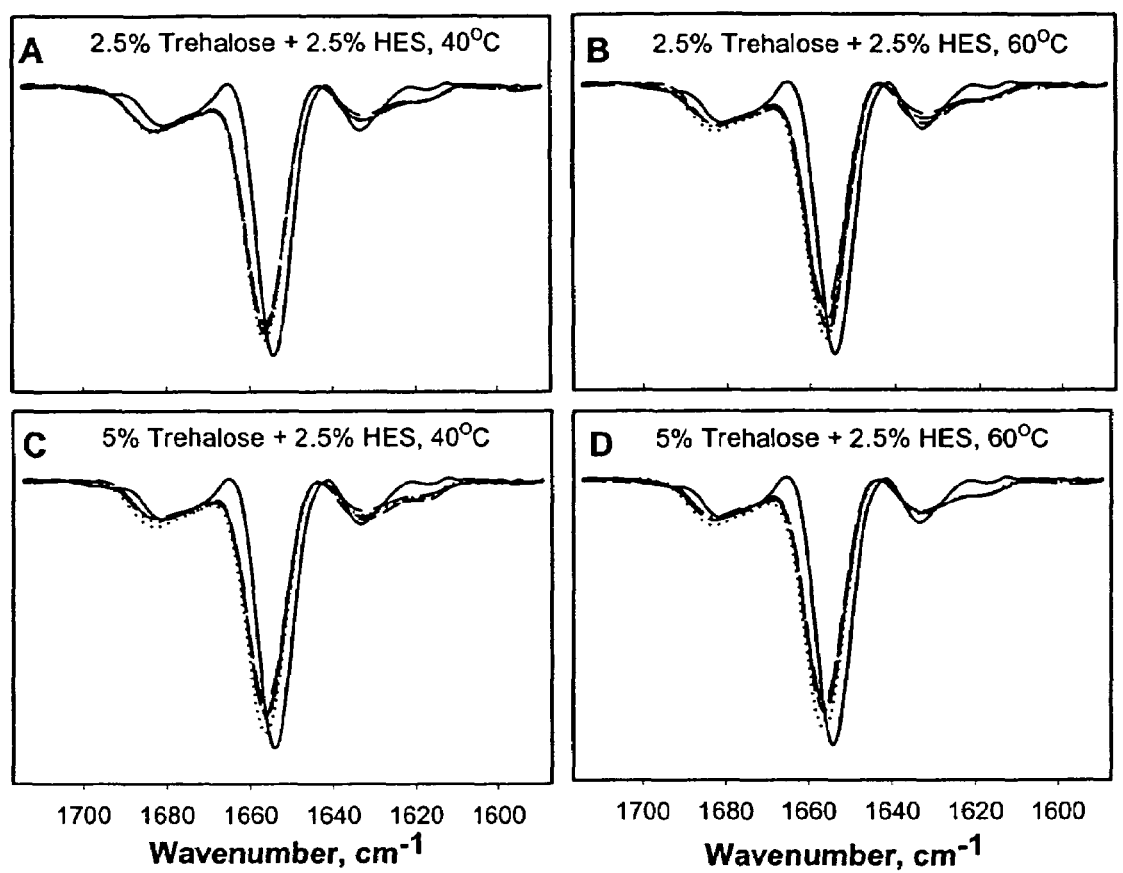
FIG. 9 is an IR spectrum plot showing the second-derivative amide I spectra of rhIL-11 dried with 2.5% trehalose plus 2.5% HES (FIGS. 9A and B) and 5.0% trehalose plus 2.5% HES (FIGS. 9C and D): (solid) native rhIL-11, (dotted) spectra taken immediately after freeze-drying, (dashed) spectra taken after 3 months, (dot-dashed) after 6 months, (long dashed) after 9 months.
Figure 10:
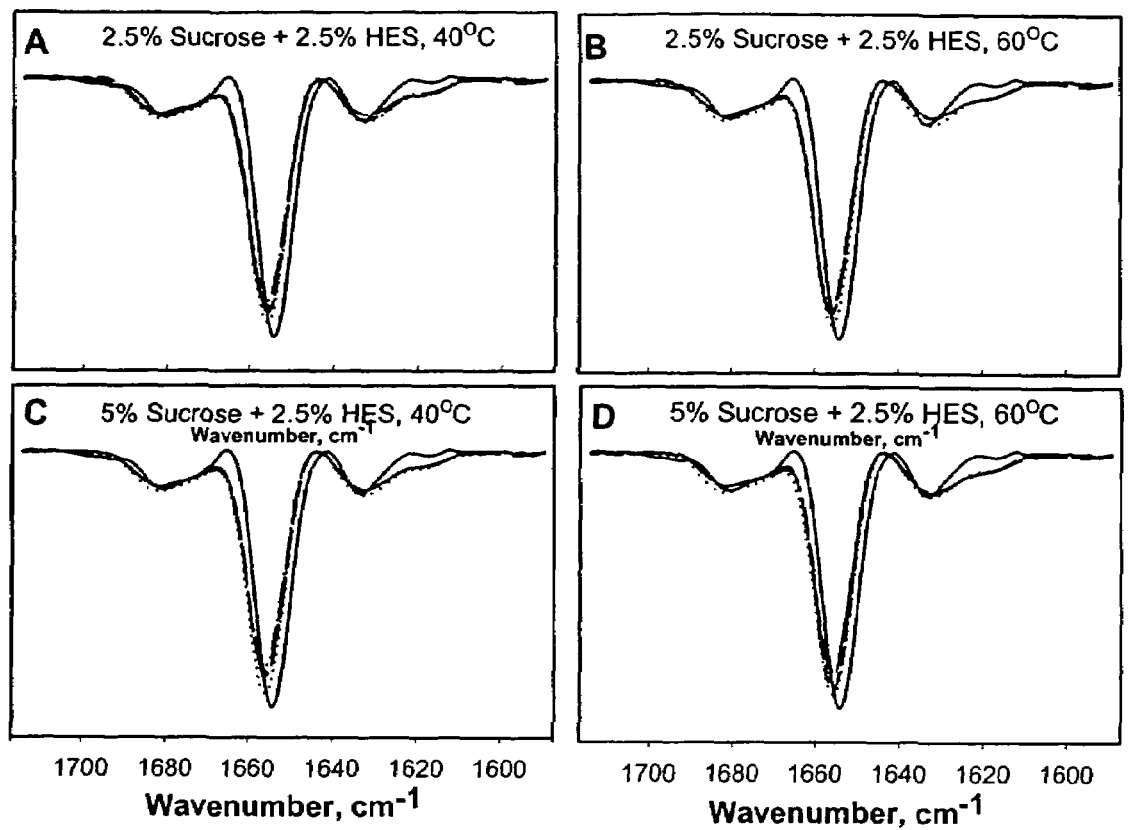
FIG. 10 is an IR spectrum plot showing the second-derivative amide I spectra of rhIL-11 dried with 2.5% sucrose plus 2.5% HES (FIGS. 10A and B) and 5.0% sucrose plus 2.5% HES (FIGS. 10C and D): (solid) native rhIL-11, (dotted) spectra taken immediately after freeze-drying, (dashed) spectra taken after 3 months, (dot-dashed) after 6 months, (long dashed) after 9 months.

Infrared spectra of rhIL-11 lyophilized in the presence of either concentration (2.5% or 5%) of trehalose showed only trivial changes during 9 months of storage at 40 or 60° C. (FIG. 7). With sucrose similar results were noted during storage at 40° C. (FIG. 8). Thus, native rhIL-11 secondary structure, which in these formulations was preserved during lyophilization, was not altered during storage in dried solid.

In contrast, during storage of the sucrose formulations at 60° C. there was a significant perturbation of secondary structure (FIG. 8) and the cakes collapsed. The infrared spectrum showed a reduction in the intensity of the native α-helix band at 1656 cm$^{-1}$ and an increase in absorbance at ca. 1618 cm$^{-1}$, which is indicative of protein aggregation. The poor storage stability noted in sucrose at 60° C. may have been due to the crystallization of the sugar. (Kreilgaard et al., J Pharm Sci. 8, 281-290 (1999); To and Flink, J Food Technol. 13, 567-581 (1978) and Hancock and Zografi, J Pharm Sci. 86, 1-12 (1997). Crystalline sucrose is anhydrous. Thus, removal of sucrose from the amorphous phase reduces the solid mass of the glass, but not the absolute amount of water present. The resulting increase in percentage water content not only reduces the glass transition temperature but also may directly contribute to protein degradation. (Hancock and Zografi, Pharm. Res. 11, 471-477 (1994)). Protein damage might also be fostered by the formation of new interfaces between sucrose crystals and the protein in the amorphous phase. (Randolph, J Pharm Sci. 86, 1198-1203 (1997)).

Storage Stability of rhIL-11 Dried with Mixtures of Disaccharides and HES

In the formulations with HES and trehalose, there was not a detectable change in rhIL-11 secondary structure during storage at either 40 or 60° C. This result is expected because the formulations with trehalose alone were also stable during storage at these temperatures. The formulations with sucrose and HES were also resistant to protein structural perturbations during storage at 40 or 60° C. HES increased the formulation $T_g$ sufficiently high that sucrose crystallization did not occur during storage at 60° C., and protein structural perturbation was avoided.

During storage of disaccharide/HES formulations at 40° C., aggregates, oxidized Met-58 and cleavage products did not increase. During storage at 60° C., aggregate formation was almost completely inhibited and oxidation of Met-68 was greatly reduced. The formation of cleavage products was also low during storage of these formulations at 60° C.

Determination of Soluble Aggregates and Degradation Products

The ability of a disaccharide and/or HES to prevent rhIL-11 aggregate formation following long-term storage was determined. Also examined was the ability of a disaccharide and/or HES to prevent oxidation of the methionine residue at position 58 of rhIL-11 and degradation of the rhIL-11 polypeptide.

Compositions were prepared containing rhIL-11 and either 2.5% HES, 2.5% sucrose, 5% sucrose, 2.5% trehalose, or 5% trehalose. Compositions were also prepared containing rhIL-11 along with 2.5% HES and 2.5% sucrose, 5% sucrose, 2.5% trehalose, or 5% trehalose. Samples were stored at 40° C. or 60° C., and the percentage of aggregate formation was examined after 1, 3, 6, and 9 months. The percent of soluble aggregates and breakdown products was determined using size exclusion high performance liquid chromatography (SEC-HPLC) and reverse phase high performance liquid chromatography (RP-HPLC).

Soluble aggregates accounted for less than 4% of all protein, with the exception of the rhIL-11 protein stored in 2.5% HES alone at 60° C. These results demonstrate that formulations of rhIL-11 lyophilized with the disaccharides alone or combined with HES showed a protective effect against soluble aggregates formation at either storage temperature.

The chemical stability of rhIL-11 during long-term storage of the proteins was examined by measuring the level of Met-58 oxidation in the preparations at the indicated temperatures. At 40° C., less than 4% of the methionine residues were oxidized for all formulations tested. At 60° C., sucrose formulations were not found to protect against Met-58 oxidation. Formulations prepared with trehalose and HES showed reduced Met-58 oxidation as compared to sucrose. Formulations of rhIL-11 lyophilized with sucrose and HES showed lower levels of Met-58 oxidation than rhIL-11 formulated with trehalose-HES formulations. HES by itself was not found to prevent Met-58 oxidation. Met-58 oxidation in HES-only formulations was higher in samples stored at 60° C. than in samples stored at 40° C.

The chemical stability of rhIL-11 during long-term storage was also examined by assaying the level of IL-11-related cleavage products. Levels of IL-11-related species were less than 3% and 10% for the disaccharide formulations stored at 40° C. or 60° C., respectively. The levels of cleavage products were slightly higher in rhIL-11 from trehalose-HES formulations as compared to cleavage products from rhIL-11 from sucrose-HES formulations. rhIL-11 formulated in 2.5% HES alone showed 12.0% and 45.0% related species after nine months storage at 40° C. and 60° C., respectively.

These data demonstrate that optimal stability was found with formulations that included both HES and either sucrose or trehalose. Including HES along with the disaccharides did not affect protein structure, but its presence did prevent aggregate formation. The disaccharides alone were more effective than HES alone at inhibiting lyophilization-induced protein unfolding.

OTHER EMBODIMENTS

Other embodiments are within the claims.

What is claimed is:

1. A composition comprising a polypeptide, a disaccharide and a hydroxyethyl starch, wherein said polypeptide does not include an N-linked glycosylation site and is stable for at least 9 months when said composition is stored at 60° C.

2. The composition of claim 1, wherein said polypeptide does not include a cysteine amino acid.

3. The composition of claim 1, wherein said polypeptide has a basic pI.

4. The composition of claim 1, wherein said disaccharide is selected from the group consisting of trehalose and sucrose.

5. The composition of claim 4, wherein said disaccharide is present at a concentration of 0.5% (wt/vol) to 6.0% (wt/vol).

6. The composition of claim 4, wherein said disaccharide is present at a concentration of 1.5% (wt/vol) to 6.0% (wt/vol).

7. The composition of claim 4, wherein said disaccharide is present at a concentration of 2.5% (wt/vol) to 5.0% (wt/vol).

8. The composition of claim 1, wherein said hydroxyethyl starch is present at a concentration of 0.5% (wt/vol) to 3.5% (wt/vol).

9. The composition of claim 1, wherein said hydroxyethyl starch is present at a concentration of 2.5% (wt/vol).

* * * * *